United States Patent [19]

Vanderhoek

[11] Patent Number: 6,077,525

[45] Date of Patent: Jun. 20, 2000

[54] USE OF CONJUGATED LINOLEIC ACIDS

[75] Inventor: Jack Y. Vanderhoek, Bethesda, Md.

[73] Assignee: The George Washington University, Washington, D.C.

[21] Appl. No.: 09/058,200

[22] Filed: Apr. 10, 1998

[51] Int. Cl.[7] .................................................. A23K 1/165
[52] U.S. Cl. ...................... 424/442; 424/441; 424/440; 424/464; 424/439
[58] Field of Search .................................. 424/442, 441, 424/440, 464, 439

[56] References Cited

U.S. PATENT DOCUMENTS

| | | | |
|---|---|---|---|
| 4,061,738 | 12/1977 | Martin | 424/195 |
| 5,017,614 | 5/1991 | Pariza et al. | 514/558 |
| 5,070,104 | 12/1991 | Pariza et al. | 514/549 |
| 5,208,356 | 5/1993 | Pariza et al. | 554/79 |
| 5,397,778 | 3/1995 | Forse et al. | 514/198 |
| 5,416,114 | 5/1995 | Yehuda | 514/560 |
| 5,428,072 | 6/1995 | Cook et al | 514/560 |
| 5,430,066 | 7/1995 | Cook et al. | 514/558 |
| 5,468,776 | 11/1995 | Yehuda | 514/560 |
| 5,585,400 | 12/1996 | Cook et al. | 514/560 |
| 5,599,840 | 2/1997 | Yehuda | 514/549 |

FOREIGN PATENT DOCUMENTS 7-41421  2/1995  Japan .

OTHER PUBLICATIONS

Setty, et al; 13–Hydroxyoctadeca–9, 11 dienoic acid (13ohode) inhibits thromboxane a2 synthesis, and stimulates 12–hete production in human platelets . . . EMBASE abstract AN 87222961, 1987.
Fujimoto, Yohko et al; Effect of 13 hydroperoxy–9,11–octadecadienoic acid (13–HPODE) on arachidonic acid metabolism in rabbit platelets . . . HCAPLUS abstract AN 1994: 182692.
Chin et al, Dietary sources of conjugated dienoic isomers of linoleic acid, a newly recognized class of . . . HCAPLUS abstract AN 1993: 100589.
Chin et al, J. Food Comp. Anal., 5:185–197 (1992).
Shanta et al, J. Am. Oil Chem. Soc., 69:(5):425–428 (1992).
Chin et al, Cancer Res., 51:6118–6124 (1991).
Singh et al, Cancer Res., 54:63–128 (1992).
Belury, Nutr. Rev., 53:83–89 (1995).
Kritchevsky et al, Atherosclerosos, 108:19–25 (1994).
Nicolosi, INFORM, Feb. 2, 1996 issue, p. 157.
Carter et al, Cancer Res., 43:3559–3562 (1983).
Smith et al, Biochemistry of Lipids, Lipoproteins and Membranes, (D.E. Vance and J. Vance Eds.), Elsevier, pp. 283–308 (1996).
Papatheofanis et al, Biochemistry of Arachidonic Acid Metabolism, (W.M.E. Lands, Ed.), M. Nijhoff Publishing, pp. 9–39 (1985).
Vanderhoek et al, J. Biol. Chem., 255:5996–5998 (1980).
Vanderhoek et al, Biochem. Pharmacol., 42:959–962 (1991).
Vanderhoek et al, Biochem. Pharmacol., 31:3463–3467 (1982).
Schoene et al, Nutr. Res., 6:75–83 (1986).
Ip et al, Nutrition and Cancer, 27(2):131–135 (1997).
MacIntyre et al, Blood, 63:848–857 (1984).
Lands et al, Advances in the Biosciences, 9:15–28.
Ford–Hutchinson, Lipoxygenases and Their Products, Chapter 6, 137–161 (1991).
Derwent Abstracts: South African Patents 9603433A and 9603360A.
Derwent Abstracts: WO 9634855.
Derwent Abstracts: EP 799033.

Primary Examiner—Neil S. Levy
Assistant Examiner—D. Faulkner
Attorney, Agent, or Firm—Pillsbury Madison & Sutro LLP

[57] ABSTRACT

The use of conjugated linoleic acid to inhibit cyclooxygenase-catalyzed conversion of arachidonic acid, thromboxane formation and platelet aggregation.

8 Claims, 5 Drawing Sheets

USE OF CONJUGATED LINOLEIC ACIDS

The invention relates to the use of conjugated linoleic acids (CLAs) to inhibit the cyclooxygenase-catalyzed conversion of arachidonic acid to thromboxane/prostanoids in platelets and platelet function, particularly platelet aggregation.

BACKGROUND OF THE INVENTION

Conjugated linoleic acids (CLAs) have received considerable attention recently because of reports that they may have chemoprotective properties.

CLAs (notably 9,11- and 10,12-octadecadienoic acids or, more simply, 9,11–18:2 or 10,12–18:2) are isomers of linoleic acid (9,12-linoleic acid). The term "CLA" is used in a generalized sense to refer to certain positional and geometrical isomers of linoleic acid, these isomers being characterized by the presence of a set of conjugated double bonds which differentiate the CLAs from the precursor linoleic acid, the latter being characterized by a non-conjugated pair of double bonds at the C-9 and C-12 positions. The CLAs are primarily the 9,11- and/or 10,12- isomers, each of which has possible cis and trans configurations at the double bonds.

CLAs have been found predominantly in meat and dairy products (1–2). CLA content is highest in ruminant meats. For example, lamb contains 6 mg of CLAs per gram of fat with smaller amounts being found in poultry and eggs. Dairy products also contain considerable amounts of CLAs. For example, homogenized milk has about 5.5 mg/g of fat.

In the past few years, CLAs have generated considerable interest in cancer and cardiovascular research. A variety of reports have appeared indicating that CLAs may be effective in inhibiting the initiation and/or post-initiation phases of carcinogenesis in several experimental animal models (3–5). CLAs have also been reported as decreasing the incidence of chemically induced skin and forestomach cancers in mice and mammary tumors in rats. Other findings indicate that CLAs have reduced in vitro cell growth when added to malignant melanoma cells, colorectal cancer cells and human breast cancer cells.

As far as the effects of CLAs on cardiovascular disease are concerned, Kritchevsky and co-workers have reported the suppression of atherosclerosis in rabbits (6). Thus, when rabbits were fed an atherogenic diet containing CLA, a decrease in total plasma- and LDL cholesterol levels was observed. In another study, Nicolosi found that addition of CLA to the diet of hamsters reduced LDL-cholesterol levels and aortic atherosclerosis (7).

Although there are probably a variety of mechanisms by which CLAs inhibit carcinogenesis and reduce cholesterol levels, none of these mechanisms has yet been conclusively identified. Previous reports have suggested that certain prostanoid inhibitors may be effective in preventing the initiation of chemical carcinogenesis (8) and, in view of this, one might speculate that CLAs function in a similar manner, possibly by preventing prostanoid formation. However, until the present invention, the use of CLAs to control prostanoid formation has not been disclosed.

Prostanoids are members of the eicosanoid family of metabolites formed from arachidonic acid (see FIG. 1). Eicosanoids are produced by most mammalian cell types and are potent cellular regulators that function as local mediators since they act at or near the location at which they are synthesized (9). For example, the eicosanoids are known to mediate induction of blood clotting and a variety of inflammatory responses.

There are two main pathways of arachidonic acid metabolism in the body. One is the so-called "cyclic" or cyclooxygenase-catalyzed pathway and a second one, the "linear" or lipoxygenase-catalyzed route [(9), FIG. 1]. The cyclic pathway generates prostanoids including prostaglandins and thromboxane, for example, thromboxane $A_2$ ($TXA_2$) which is a very potent inducer of platelet aggregation. The lipoxygenase-mediated pathway, on the other hand, produces hydroperoxy derivatives of arachidonic acid. A variety of cells can produce the 5-hydroperoxy metabolite which is the precursor of the leukotriene group of substances that are potent contractors of vascular smooth muscle and constrictors of lung bronchi.

Several prior studies have shown that different fatty acids can act as competitors of both the cyclooxygenase and lipoxygenase enzymes (10). However, it appears that there has been no study regarding the activity of CLAs with respect to these enzymes.

SUMMARY OF THE INVENTION

The invention is based, at least in part, on the finding that CLAS, notably 9,11–18:2 and 10,12–18:2, and hydroxy derivatives thereof, selectively inhibit the cyclooxygenase-catalyzed conversion of arachidonic acid into thromboxane/prostanoids. According to the invention, the CLAs do not affect the lipoxygenase-catalyzed pathway. As a consequence, the invention contemplates the use of CLAs to inhibit platelet thromboxane formation or platelet aggregation. As indicated, this activity of the CLAs appears to be specific to inhibition of the cyclooxygenase activity with respect to the conversion of arachidonic acid to thromboxane and prostanoids with consequent restriction on the tendency of platelets to aggregate. The CLAs appear to be selective in this respect and do not seem to inhibit, or otherwise effect, the other pathways of arachidonic acid metabolism.

The above-noted selective action of CLAs on the cyclooxygenase-catalyzed conversion of arachidonic acid indicates that the administration of effective amounts of a CLA, for example, as an additive to food or in pharmaceutical form, to mammals can provide a useful method for treating thrombic conditions by inhibiting the cyclooxygenase-catalyzed conversion of arachidonic acid to thromboxane. In a more specific aspect, the invention provides a method for inhibiting platelet aggregation by administering an effective amount of a CLA or mixture thereof to a mammal in need of such inhibition. Other aspects of the invention will be evident from the description which follows.

DESCRIPTION OF PREFERRED EMBODIMENTS

Figure 1:
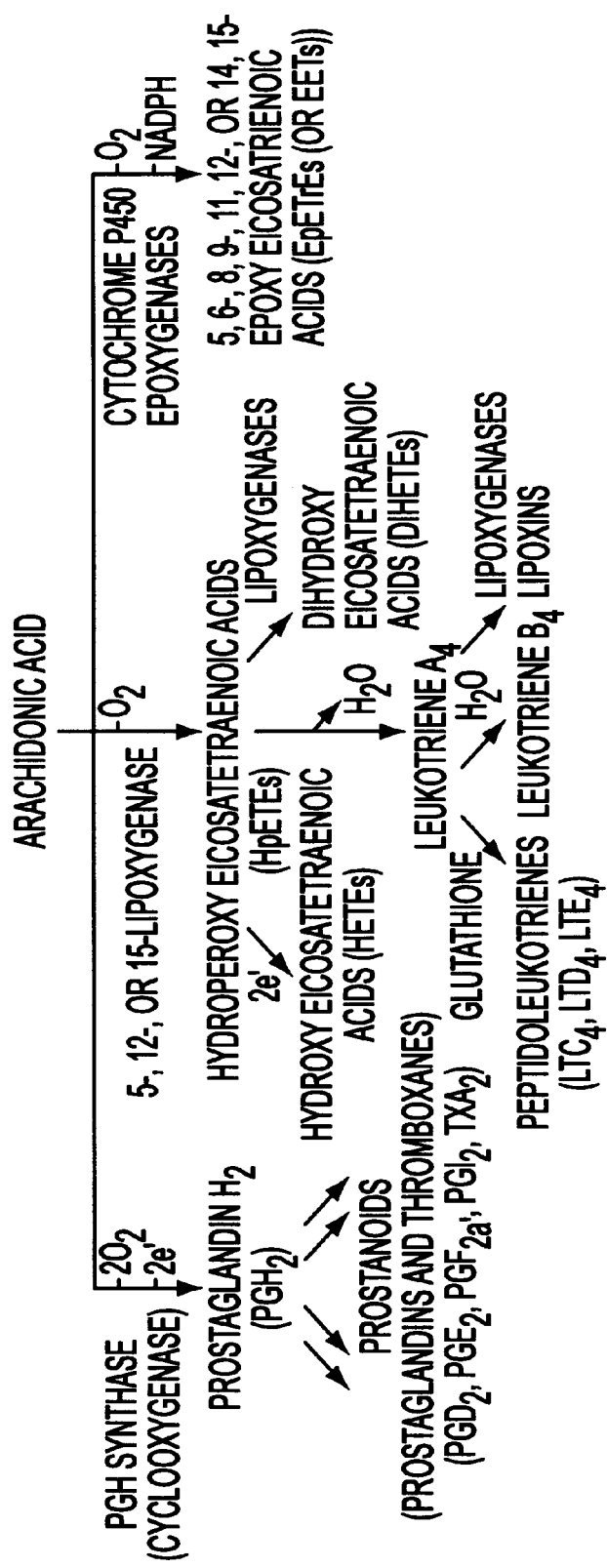
FIG. 1 illustrates the cyclic and non-cyclic pathways of arachidonic acid metabolism.

The CLAs useful herein advantageously comprise 9,11- and 10,12-octadecadienoic acid which, as earlier noted, may also be called 9,11–18:2 or 10,12–18:2, respectively, or the hydroxy derivatives thereof. These CLAs may be used separately, or in admixture, in either the cis- and/or trans-forms. It does not appear essential to use the 9,11–18:2 and/or 10,12:18-2 isomers in pure form provided these isomers represent the major component of the composition which is used. Advantageously, a mixture comprising 9c,11t and 10t,12c is used in the amounts of 5–95% by weight of each isomer. Preferably a mixture comprising 55–85% by weight of 9c, 11t isomer and 45–15% 10t, 12c, or vice versa, is used.

As one representative CLA composition suitable for use herein, there may be mentioned the following where percents are by weight:

CLA Composition ("CLA mix")

18% oleic acid

6% palmitic acid

31% 9c, 11t and 9t, 11c-isomers

33% 10t, 12c and 11c, 12t-isomers 2.3% 9c, 11c, and 10c, 12c-isomers

2% other (i.e. diglycerides)

A pure form of the 9,11-isomer is also commercially available and may be used for present purposes.

As indicated, hydroxy derivatives of the 9,11 - and/or 10,12-isomers may also be used. For example, the 13-hydroxy and 9-hydroxy derivative of 9,11–18:2 and 10,12–18:2, respectively (referred to herein as 13- or 9-HODE) are suitable for use. Of these hydroxy derivatives, it is noted that 13-HODE is more potent as a thromboxane inhibitor than the parent 9,11–18:2 while 9-HODE is less potent than the corresponding non-hydroxylated parent 10,12–18:2. As indicated earlier, the finding that 9,11–18:2 and 10,12–18:2 and their hydroxylated derivatives, inhibit thromboxane formation and consequently platelet aggregation appears to be specific to the CLAs.

For ease of reference, it is noted that isomeric structures of linoleic acid; CLA 9,11–18:2; and 10, 12–18:2; and 13-HODE are set out below:

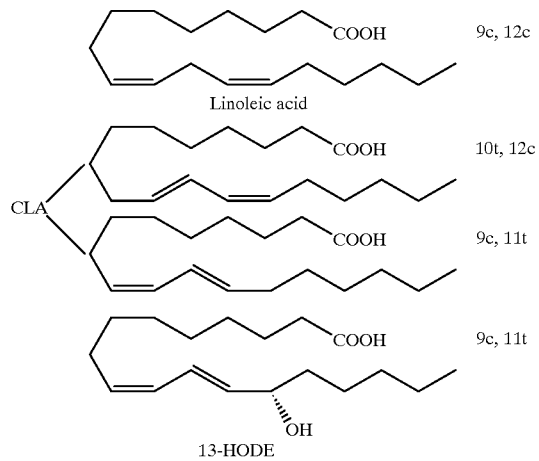

As indicated, the invention contemplates the addition of the CLA to food or as an active component in a pharmaceutical composition of conventional form, e.g. a tablet, capsule or equivalent. The CLA may be added to any type of food, e.g. butter or other spreads, bread or the like. When used in pharmaceutical form, the CLA may be the only active component or it may be used in combination with one or more other pharmaceutically effective agents.

The amount of CLA used to inhibit platelet aggregation or the cyclooxygenase-catalyzed conversion of arachidonic acid to thromboxane (TX) can be widely varied depending on other factors, e.g. body weight. However, the amount of CLA to be administered can be readily determined for any specific situation. Generally, however, the amount of CLA used will be in the range of 0.25 to 0.5 grams as a daily dose per kg of mammal being treated.

The invention is illustrated by the following examples:

EXAMPLE 1

This example illustrates the effects of CLA on platelet thromboxane formation.

Human platelets were isolated from donors according to previously established procedures (13) and resuspended in Krebs-Henseleit buffer (pH 7.4) at a concentration of $3 \times 10^8$ platelets/ml. The platelets (0.5 ml) were placed in a 37° C. water bath for several minutes and then treated with either vehicle (ethanol) or various concentrations of the fatty acid to be tested for 2 min. Next, 10 $\mu$M (final concentration) [$^{14}$C]-arachidonic acid was added. In some experiments, 20 $\mu$M calcium ionophore A23187 was added about 5 sec. prior to the addition of the arachidonic acid substrate. Ten minutes after the addition of arachidonic acid, the reaction was terminated with 10% formic acid and the products extracted with chloroform-methanol. Product separation and analysis by thin layer chromatography (TLC) was carried out as previously described using unlabeled arachidonic acid, 15-HETE and thromboxane $B_2$ as standards (11). The various radioactive product and unreacted substrate bands were visualized by autoradiography and quantitated either by scraping the bands from the TLC plate and counting the samples in a liquid scintillation counter or by determining the relative band intensities using a Personal Densitometer SI (Molecular Dynamics, Sunnyvale, Calif.) with ImageQuaNT v4.2 software).

Figure 2:
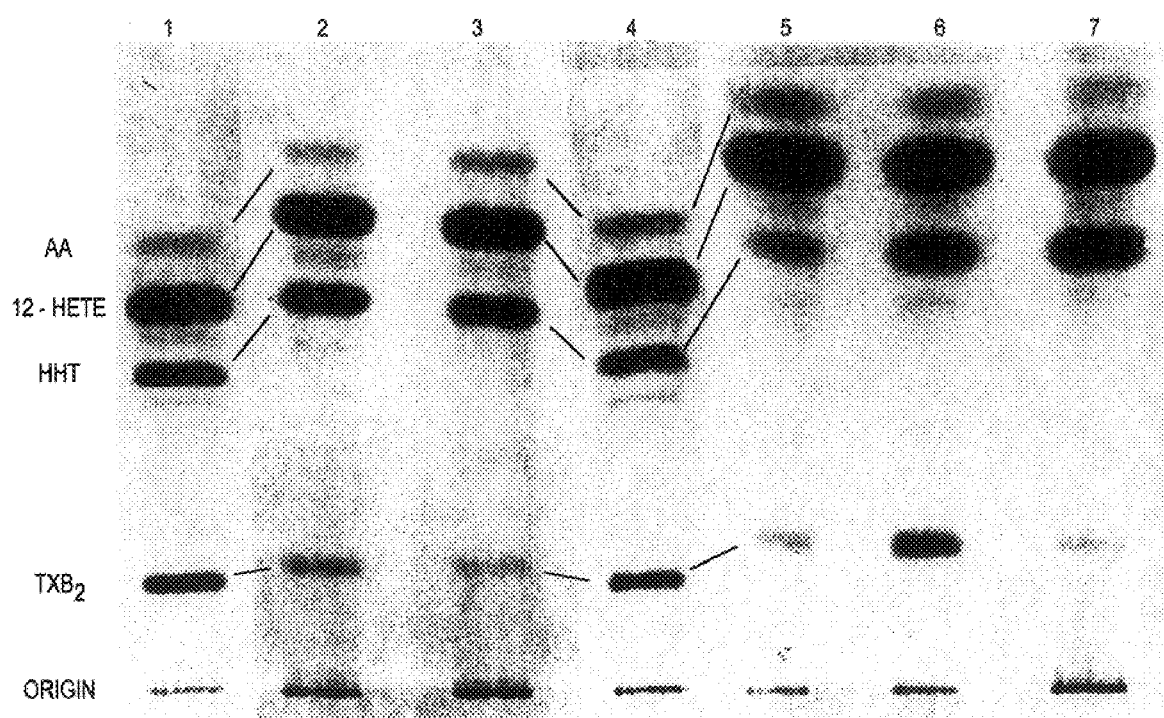
FIG. 2 is an autoradiograph of platelet arachidonic acid metabolites (separated by thin layer chromatography) formed in the absence or presence of various CLA isomers.

As shown in FIG. 2, lane 1, the major arachidonate metabolites formed by platelets are two cyclooxygenase metabolites, i.e. thromboxane $B_2$ ($TXB_2$) and 12-hydroxyheptadecatrienoic acid (HHT), and the lipoxygenase metabolite 12-hydroxyeicosatetraenoic acid (12-HETE). When platelets were incubated with various concentrations of either CLA mix (containing 31% 9,11–18:2 and 33% 10,12–18:2, lanes 2 and 3), 9,11–18:2 (lanes 4 and 5), 10,12–18:2 (lanes 6 and 7), $TXB_2$ was inhibited with no effect on the 12-HETE production. Hence, formation of the cyclooxygenase product $TXB_2$, but not the 12-lipoxygenase metabolite, was sensitive to CLA inhibition.

To obtain the results shown in FIG. 2, the human platelets were pretreated with the various concentrations of CLA isomers followed by the addition of calcium ionophore A23187 and [$^{14}$C]-arachidonic acid. Products were isolated, separated by thin layer chromatography as described above. The results shown in FIG. 2 are from a typical experiment wherein lane 1- represents platelets treated with ethanol (vehicle), lane 2-platelets treated with 3 $\mu$M CLA mix (31% 9,11–18:2 and 33% 10,12–18:2), lane 3- platelets treated with 10 $\mu$M CLA mix (31% 9,11–18:2 and 33% 10,12–18:2), lane 4-platelets treated with 30 $\mu$M 9,11–18:2, lane 5- platelets treated with 60 $\mu$M 9,11–18:2, lane 6- platelets treated with 3 $\mu$M 10,12–18:2 and lane 7-platelets treated with 10 $\mu$M 10,12–18:2. The identities of the bands in decreasing order of Rf are as follows: AA-unreacted arachidonic acid, 12-HETE-12-hydroxyeicosatetraenoic acid (a platelet 12-lipoxygenase metabolite), HHT-12-hydroxyheptadecatrienoic acid, $TXB_2$-thromboxane $B_2$, the latter two products are cyclooxygenase metabolites, origin-sample application point.

Figure 3:
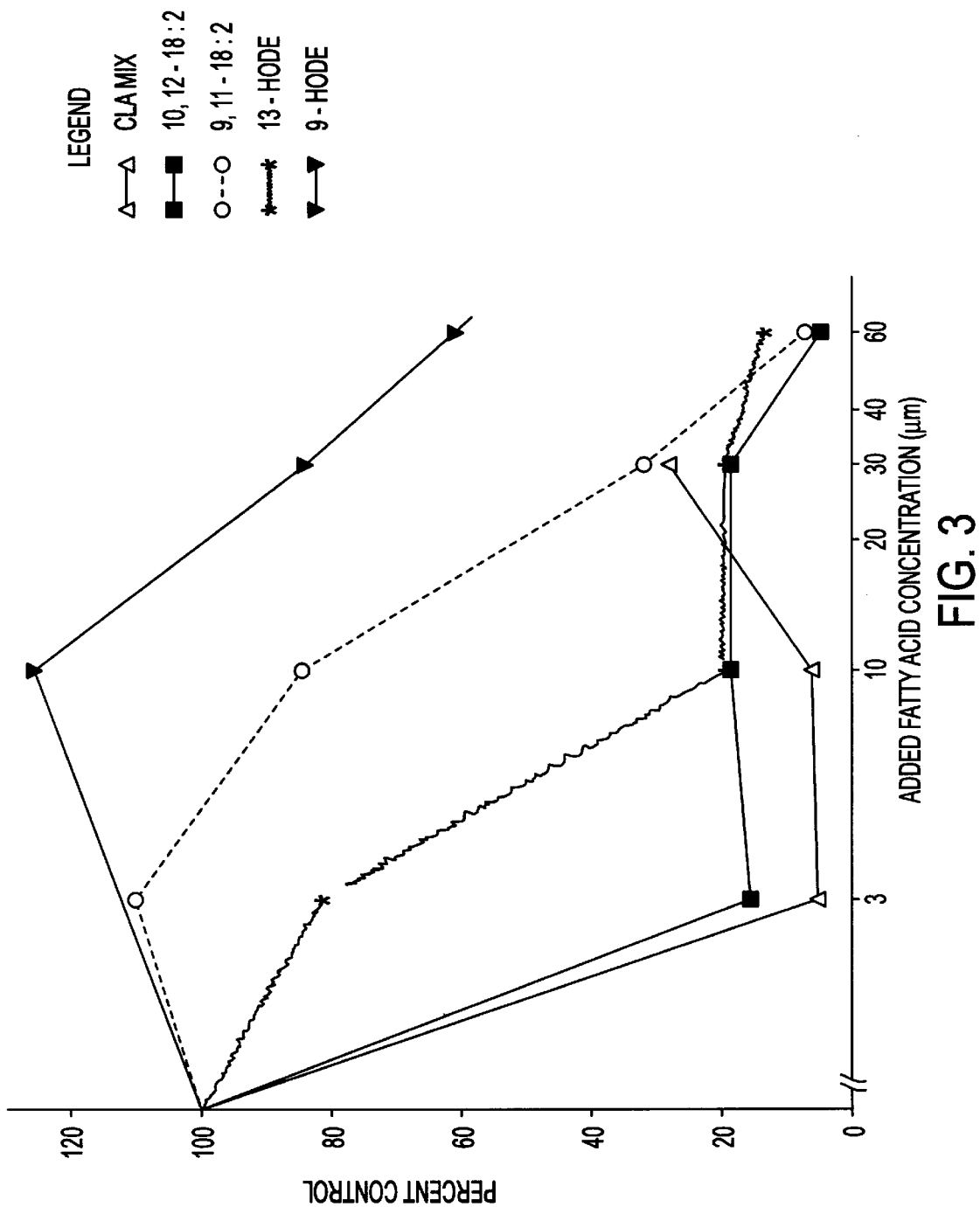
FIG. 3 is a dose response curve of various CLA isomers on platelet thromboxane formation.

A typical dose response curve of these isomers as well as the hydroxylated analogs 9-HODE (10,12 double bond isomer) and 13-HODE (9,11 double bond isomer) is shown in FIG. 3. The data shown were obtained by determining the effects of various concentrations of CLA isomers on platelet thromboxane $B_2$ production. Control platelets (ethanol vehicle) from the donor converted 12% of [$^{14}$C]-arachidonic acid to [$^{14}$C]-thromboxane $B_2$. [$^{14}$C]-thromboxane $B_2$ production by fatty acid-treated platelets relative to vehicle-treated platelets was determined and expressed as % control. Symbols used for various fatty acids: ▲▲, CLA mix ■-■, 10,12–18:2, ○-○, 9,11–18:2, *-*, 13-HODE, ▽-▽, 9-HODE.

Table 1 shows the inhibitory effect of CLA mix (9,11–18:2; 10,12–18:2) as used herein on human platelet thromboxane and 12-HETE formation as determined by radioactive product distribution in the control platelets and those treated with CLA mix.

TABLE 1

| Sample | % DPM Thromboxane ($TXB_2$) Formation | 12-HETE Formation |
| --- | --- | --- |
| control (no CLA) | 9.2 | 59.6 |
| CLA (10 μM) | 7.0 | 63.7 |
| CLA (30 μM) | 3.0 | 67.6 |
| CLA (60 μM) | 4.9 | 66.4 |

It is concluded from the data given in Table 1 that CLA (9,11–18:2; 10,12–18:2 mix) inhibits thromboxane $TXB_2$ formation while the CLA has no significant effect on 12-lipoxygenase.

Table 2 below summarizes the inhibitory potencies of the various CLA isomers tested. The results show that the inhibitory effectiveness of the CLA mix as well as the pure 9,11- and 10,12–18:2 isomers on platelet $TXB_2$ formation was approximately the same. The introduction of a hydroxyl functionality into the 9,11 isomer, i.e. 13-HODE, enhanced its inhibitory potency relative to the non-hydroxylated analog about five fold whereas the addition of a hydroxyl group into the 10,12-isomer, i.e. 9-HODE, decreased the inhibitory effectiveness more than two fold relative to 10,12–18:2.

TABLE 2

Summary of Inhibitory Potencies of Various CLA Isomers on Human Platelet Thromboxane Production

| Fatty Acid | Inhibitory Potency ($I_{50}$, μM)[1] |
| --- | --- |
| CLA mixture | 9.1 ± 2.6 (11)[2] |
| 9c, 11t-18:2 | 16 ± 1.8 (7) |
| 10t, 12c-18:2 | 13 ± 4.1 (7) |
| 9-HODE (10t, 12c isomer) | 34 ± 6.5 (7) |
| 13-HODE (9c, 11t isomer) | 3.0 ± .7 (6) |
| Oleic acid | >60 |

[1]$I_{50}$ is the fatty acid concentration that inhibits platelet thromboxane formation (from exogenously added arachidonic acid in the presence of calcium ionophore A23187) by 50% and is given as the mean ± S.E.M.
[2](n) = number of donors tested.

Statistical analysis using the Student test, indicates that the difference in $I_{50}$s between 9,11–18:2 and 13-HODE, between 10,12–18:2 and 9-HODE, and CLA mix and 9,11–18:2 is statistically significant (p<0.05) but that there were no statistically significant differences between CLA mix and 10,12–18:2 and between 9,11–18:2 and 10,12–18:2.

The CLA mix, 9,11–18:2 and 10,12–18:2 used in the foregoing examples are available (Unilever Research Labs) while the 9-HODE and 13-HODE (9c,11t) were obtained from Cayman Chemical Company, Ann Arbor, Mich.

EXAMPLE 2

This example illustrates the effects of CLA on rat platelet aggregation.

Rat platelets were isolated and resuspended at a concentration of $2 \times 10^8$ platelets/ml Tyrodes buffer (pH 7.3) as previously described (14). Aggregation studies were carried out in a dual-channel aggregometer (ChronoLog Co., Havertown, Pa.). Platelets were pretreated with various concentrations of CLA mix for 1 min. And aggregation induced by the addition of 20 μM sodium arachidonate in the presence of 1 mM $CaCl_2$.

Figure 4:
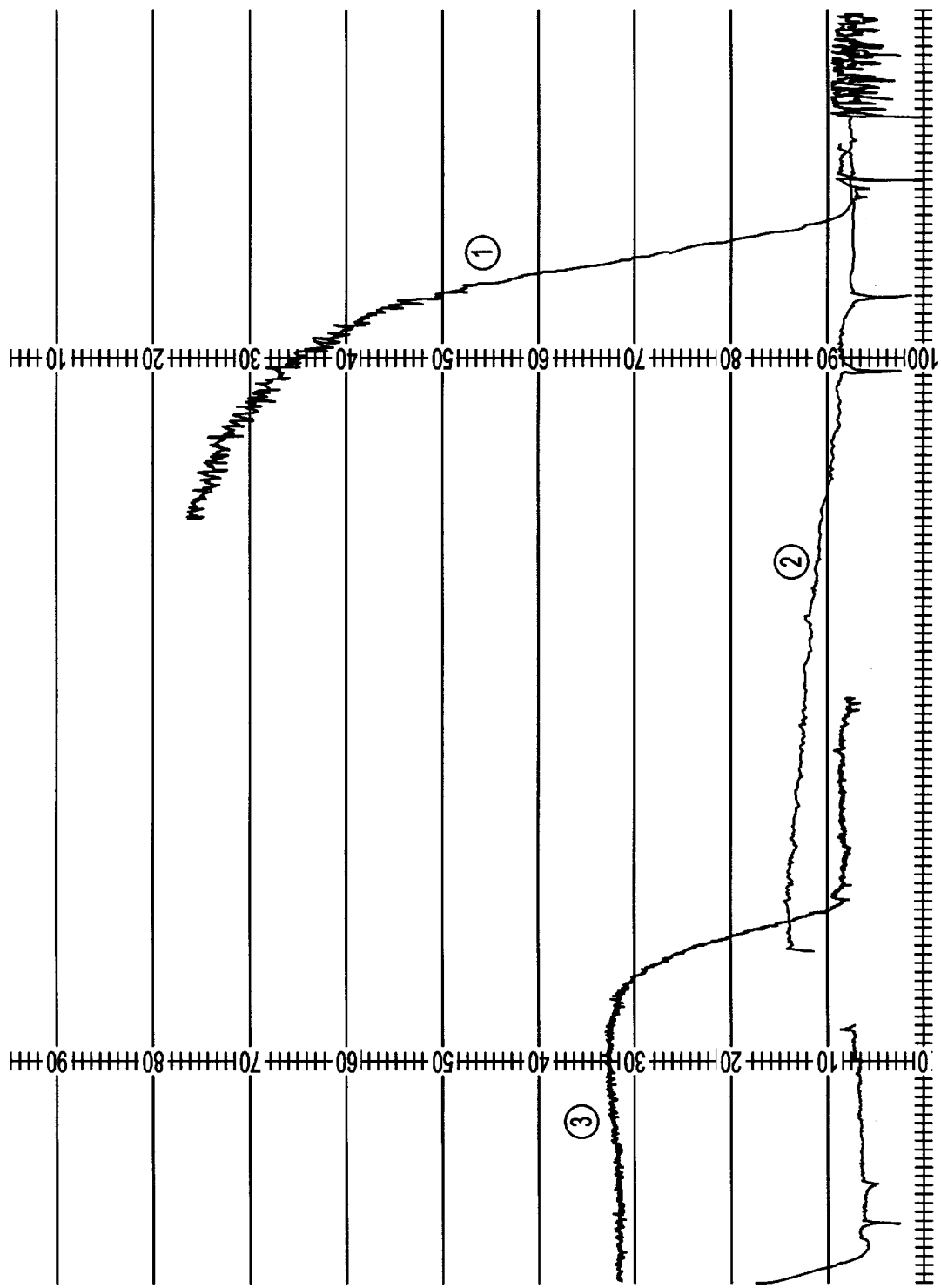
FIG. 4 is a graph illustrating the antiaggregatory effect of CLAs on rat platelet aggregation.

The effect of the CLA mix on platelet aggregation was examined and the results shown in FIG. 4 indicate that 50 and 100 μM CLA mix inhibited rat platelet aggregation induced by sodium arachidonate.

The rat platelets utilized in this example, the results of which are shown in FIG. 4, were pretreated with either vehicle (ethanol) or several concentrations of CLA mix. Aggregation was induced by sodium arachidonate as described above. Curve 1 represents the results obtained with the control (ethanol vehicle), while curve 2 and curve 3 plot the results obtained, respectively, with platelets pretreated with 100 μM CLA mix and with platelets pretreated with 50 μM CLA mix.

The relative effectiveness of the CLA mix and linoleic acid on human platelet aggregation induced by four different agonists, i.e. arachidonic acid, collagen, thrombin and ionophore (A29187), was examined. The agonists tested are known to activate platelets via different mechanisms. Thus, collagen and thrombin are thought to interact with specific receptors whereas ionophore bypasses the receptor-occupancy stage of the platelet activation process and arachidonic acid is converted to the potently aggregatory thromboxane A2.

Figure 5:
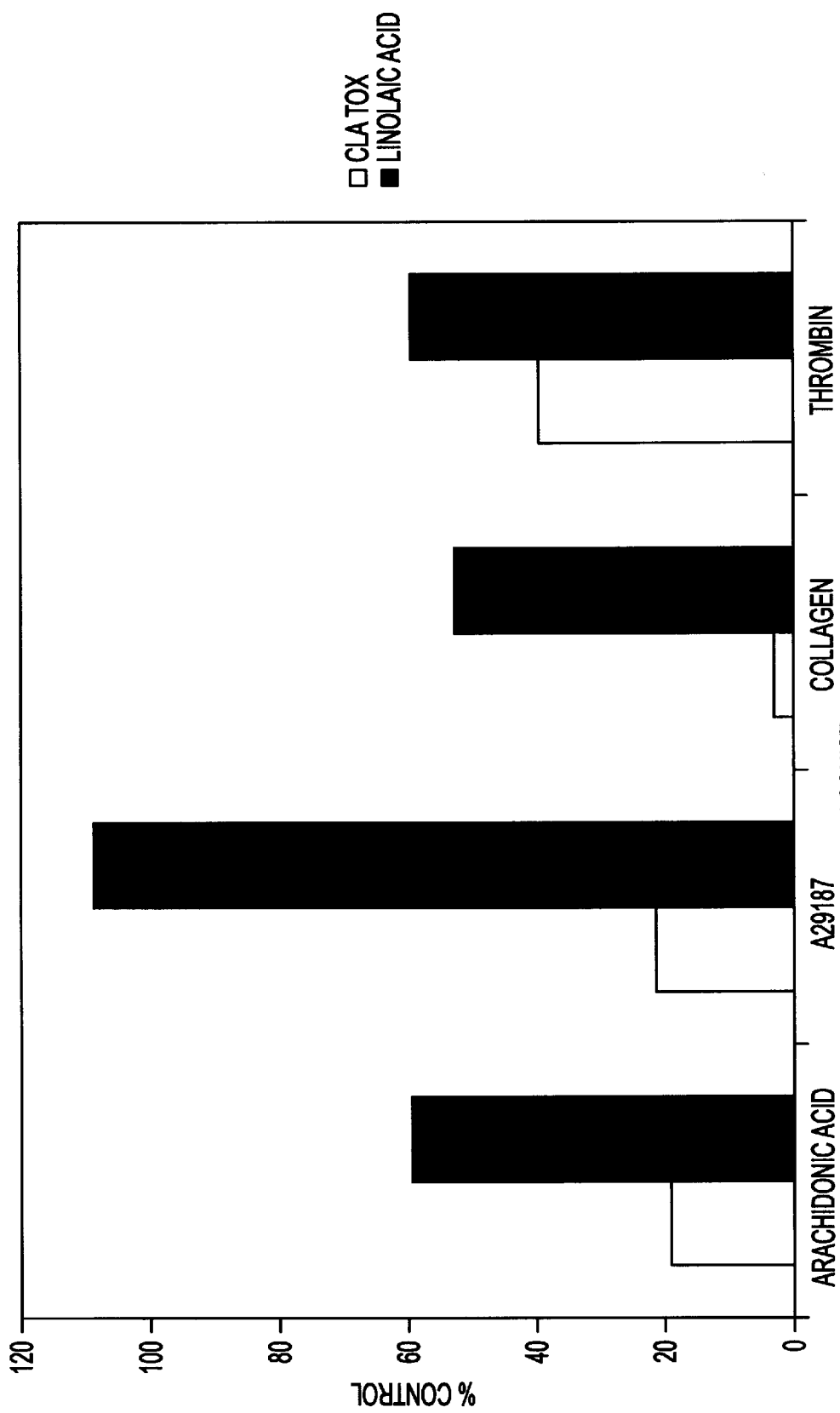
FIG. 5 is a graph illustrating the relative inhibitory effectiveness of CLA and linoleic acid (LA) on platelet aggregation.

The results shown in FIG. 5 indicate that with all aggregating agents tested, the CLA mix inhibited platelet aggregation more effectively than the same concentration of linoleic acid. The difference in inhibitory effectiveness of these two acids was most pronounced with collagen and least with thrombin. Although the relative effectiveness of these two fatty acids was found to be the same with three other donors, some differences in agonist sensitivity were observed. These results confirm the importance of conjugated double bonds in linoleic acid in inhibiting platelet aggregation.

As will be evident from the foregoing, CLA has an important antithrombotic role in inhibiting the cyclooxygenase pathways and consequent inhibition of platelet function or aggregation.

This inhibiting function of CLA may be utilized in a variety of ways, for example, as an additive to food. The following example illustrates how the invention may be used to provide a healthy spread.

EXAMPLE 3

A low-fat spread having a fat content of about 60% is prepared by combining equal parts of W/O Emulsion A of a temperature of 17° C. and W/O Emulsion B of a temperature of 20° C. in a surface-scraped heat exchanger (Votator A unit) in which the combined emulsion is cooled to 0° C. The emulsion obtained is mildly agitated, further crystallized in a post-crystallizer unit (Votator B unit) and packed at 17° C.

Emulsions A and B are separately prepared by blending and emulsifying fatty and aqueous ingredients in separate vessels and cooling the emulsions in scraped-surface heat exchangers to the temperature indicated.

The emulsions are composed of (wt %):

|  | A | B |
|---|---|---|
| Water | 35.47 | 38.08 |
| Salt | 1.89 | 2.0 |
| Dicalcium phosphate | 0.34 | — |
| Sodium citrate | 0.38 | — |
| Glucose | 0.89 | — |
| Sodium alginate | 0.64 | — |
| Glucono-delta lactons | 0.47 | — |
| Oil blend | 59.68 | 59.68 |
| Distilled monoglycerides from lard | 0.2 | 0.2 |
| Colour | 0.02 | 0.02 |
| Flavour | 0.02 | 0.02 |

The finely powdered dicalcium phosphate has an average particle size less than 1 micron. The oil blend includes 10 wt. % 9,11 octadeca dienoic acid. The oil blend, prior to the addition of the 9,11 compound, has a dilatation value of 250 at 10° C. and 25 at 35° C.

References

The references mentioned earlier are more fully identified as follows:

1. S. F. Chin, W. Liu, J. M. Storkson, Y. L. Ha and M. W. Pariza, Dietary sources of conjugated dienoic isomers of linoleic acid, a newly recognized class of anticarcinogens, *I. Food Comp. Anal.*, 5:185–197 (1992).
2. N. C. Shanta, E. A. Decker and Z. Ustunol, Conjugated linoleic acid concentration in processed cheese, *J. Am. Oil Chem. Soc.*, 69:425–428 (1992).
3. C. Ip, S. F. Chin, J. A. Scimeca and M. W. Pariza, Mammary Cancer prevention by conjugated dienoic derivative of linoleic acid, *Cancer Res.*, 51:6118–6124 (1991).
4. C. Ip, M. Singh, H. J. Thompson and J. A. Scimeca, Conjugated linoleic acid suppresses mammary carcinogenesis and proliferative activity of the mammary gland in the rat, *Cancer Res.*, 54:63–128 (1992).
5. M. A. Belury, Conjugated dienoic linoleate: a polyunsaturated fatty acid with unique chemoprotective properties, *Nutr. Rev.*, 53:83–89 (1995).
6. K. M. Lee, D. Kritchevsky and M. W. Pariza, Conjugated linoleic acid and atherosclerosis in rabbits, *Atherosclerosos*, 108:19–25 (1994).
7. R. J. Nicolosi, cited in INFORM, Feb. 2, 1996 issue, p. 157
8. See, for example, C. A. Carter, R. J. Milholland, W. Shea and M. M. Ip, Effect of prostaglandin synthetase inhibitor indomethacin on 7,12-dimethylbenz(a) anthracene-induced mammary tumorigenesis in rats fed different levels of fat, *Cancer Res.*, 43:3559–3562 (1983).
9. See, for example, W. L. Smith and F. A. Fitzpatrick, The eicosanoids: cyclooxygenase, lipoxygenase and epoxygenase pathways in *Biochemistry of Lipids, Lipoproteins and Membranes*, (D. E. Vance and J. Vance Eds), Elsevier, pp. 283–308 (1996).
10. See, for example, F. J. Papatheofanis and W. E. M. Lands, Lipoxygenase mechanisms in *Biochemistry of Arachidonic Acid Metabolism*, (W. M. E. Lands, ed), M. Nijhoff Publishing, pp. 9–39 (1985).
11. J. Y. Vanderhoek, R. W. Bryant and J. M. Bailey, 15-Hydroxy-5,8,11, 13-eicosatetraenoic acid: a potent, elective platelet lipoxygenate inhibitor, *J. Biol. Chem.*, 255:5996–5998 (1980).
12. J. Y. Vanderhoek, N. W. Schoene and P. P. T. Phan, The inhibitory potencies of fish oil hydroxy fatty acids on cellular lipoxygenases and platelet aggregation, *Biochem, Pharmacol.*, 42:959–962 (1991).
13. J. Y. Vanderhoek, R. W. Bryant and J. M. Bailey, Regulations of leukocyte and platelet lipoxygenases by hydroxyeicosanoids, *Biochem. Pharmacol.*, 31:3463–3467(1982).
14. N. W. Schoene, V. C. Morris and O. A. Levander, Altered aracidonic acid metabolism in platelets and aortas from selenium-deficient rats, Nutr. Res., 6:75–83 (1986).

It will be appreciated that various modifications may be made in the invention as described above without departing from the invention as defined in the following claims wherein:

We claim:

1. A method of inhibiting the cyclooxygenase-catalyzed conversion of arachidonic acid to thromboxane in cells which comprises contacting said cells with an effective amount of a conjugated linoleic acid selected from the group consisting of 10,12-octadeca-dienoic acid; 9,11-octadecadienoic acid and a mixture of conjugated linoleic isomers which includes at least one of 10,12-octadeca-dienoic acid or 9,11-octadecadienoic acid.

2. A method according to claim 1 of inhibiting the cyclooxygenase-catalyzed conversion of arachidonic acid to thromboxanie in a subject in need of such inhibition which comprises administering to said subject an effective amount of conjugated linoleic acid selected from the group consisting of 10,12-octadeca-dienoic acid; 9,11-octadecadienoic acid and a mixture of conjugated linoleic isomers which includes at least one of 10,12-octadeca-dienoic acid or 9,11-octadecadienoic acid.

3. A method according to claim 1 for inhibiting thromboxane formation and platelet aggregation which comprises administering to a subject in need of such inhibition, an effective amount of a conjugated linoleic acid selected from the group consisting of 10,12-octadeca-dienoic acid; 9,11-octadecadienoic acid and a mixture of conjugated linoleic isomers which includes at least one of 10,12-octadeca-dienoic acid or 9,11-octadecadienoic acid.

4. A method according to claim 1, 2 or 3, wherein the conjugated linoleic acid comprises a mix of 9,11- and 10,12-octadecadienoic acids.

5. A method according to claim 1, 2 or 3, wherein the conjugated linoleic acid is 9,11-octadecadienoic acid.

6. A method according to claim 1, 2 or 3, wherein the conjugated linoleic acid is 10,12-octadecadienoic acid.

7. A food composition comprising bread or spread having added thereto at least one conjugated linoleic acid selected from the group consisting of 9,11-octadecadienoic acid, 10,12-octadecadienoic acid and a mixture of conjugated linoleic isomers which includes at least one of 9,11-octadecadienoic acid or 10,12-octadeca-dienoic acid, the acid being present in an amount sufficient to assist in inhibiting thromboxane formation.

8. A pharmaceutical composition in tablet or capsule form for use in inhibiting thromboxane formation which comprises, as the active component, an effective amount of at least one conjugated linoleic acid selected from the group consisting of 9,11-octadecadienoic acid, 10,12-octadecadienoic acid and a mixture of conjugated linoleic isomers which includes at least one of 9,11-octadecadienoic acid or 10,12-octadeca-dienoic acid, together with a pharmaceutically acceptable carrier.

* * * * *